United States Patent
Flosser et al.

(10) Patent No.: US 9,394,224 B2
(45) Date of Patent: Jul. 19, 2016

(54) TRANSESTERIFICATION PROCESS

(71) Applicant: Rohm and Haas Company, Philadelphia, PA (US)

(72) Inventors: David A. Flosser, Missouri City, TX (US); Philippe P. Maillot, Kingwood, TX (US); Nawal K. Sharma, League City, TX (US); Alejandro Ceron, La Porte, TX (US); Mingyu Ye, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/382,687

(22) PCT Filed: Feb. 11, 2013

(86) PCT No.: PCT/US2013/025524
§ 371 (c)(1),
(2) Date: Sep. 3, 2014

(87) PCT Pub. No.: WO2013/137997
PCT Pub. Date: Sep. 19, 2013

(65) Prior Publication Data
US 2015/0045578 A1  Feb. 12, 2015

Related U.S. Application Data

(60) Provisional application No. 61/611,279, filed on Mar. 15, 2012.

(51) Int. Cl.
*C07C 67/02* (2006.01)
*C07D 233/34* (2006.01)

(52) U.S. Cl.
CPC .............. *C07C 67/02* (2013.01); *C07D 233/34* (2013.01); *Y02P 20/582* (2015.11)

(58) Field of Classification Search
CPC .... C07C 67/02; C07D 233/34; C07D 251/20; C09K 11/06; H01L 51/50; Y02P 20/582
See application file for complete search history.

(56) References Cited

U.S. PATENT DOCUMENTS

| | | | |
|---|---|---|---|
| 4,981,973 A | 1/1991 | Murray | |
| 5,072,027 A | 12/1991 | Kobayashi et al. | |
| 5,504,243 A | 4/1996 | Sakamoto et al. | |
| 5,610,313 A | 3/1997 | Riondel et al. | |
| 6,509,494 B1 | 1/2003 | Weir | |
| 7,528,278 B2 * | 5/2009 | Benderly | ................. B01J 27/10 560/217 |
| 2006/0173191 A1 | 8/2006 | Curtis | |
| 2008/0214858 A1 | 9/2008 | Yurugi et al. | |

FOREIGN PATENT DOCUMENTS

| | | |
|---|---|---|
| DE | 102005039536 | 2/2007 |
| EP | 453638 | 10/1991 |
| WO | 2013004767 | 1/2013 |

OTHER PUBLICATIONS

Barton, et al., "Partitioned polymerization, 3 a). On the use of inhibitors partially soluble in the aqueous phase", Makromol. Chem. 190, 769-775 (1989).

Gmehling, et al; Handbook of Chemistry and Physics, 96th Edition (2015-2016), 6-210-214.

* cited by examiner

*Primary Examiner* — Yevegeny Valenrod
*Assistant Examiner* — Blaine G Doletski
(74) *Attorney, Agent, or Firm* — Edward L. Brant

(57) ABSTRACT

A transesterification process produces a (meth)acrylate ester product from a mixture comprising an alkyl(meth)acrylate reactant, an alcohol reactant, a catalyst, and a polymerization inhibitor, wherein the water content in the reaction zone at the start of the transesterification step is from 0.2 to 1.1 weight percent, based on the weight of the materials in the reaction zone. The mixture is subjected to reaction conditions sufficient to produce a product (meth)acrylate and a product alcohol, which are different than the reactants.

9 Claims, No Drawings

TRANSESTERIFICATION PROCESS

CROSS-REFERENCE TO RELATED APPLICATIONS

This application claims priority from provisional application Ser. No. 61/611,279, filed Mar. 15, 2012, which is incorporated herein by reference in its entirety.

BACKGROUND OF THE INVENTION

The invention relates to a transesterification process for the production of acrylic ester monomers from alkyl (meth)acrylates and alcohols.

The transesterification reaction between alcohols and alkyl (meth)acrylates is known and commercially practiced. As typically conducted in commercial scale processes, the (meth)acrylate reactant and the catalyst are recycled.

U.S. Pat. No. 5,610,313 discloses a process for the preparation of alkyl imidazolidone (meth)acrylates that employs, as a catalyst, a mixture formed of (a) at least one magnesium alkoxide and (b) a component chosen from the chelates of calcium with 1,3-dicarbonyl compounds, dialkyltin oxides, dialkyltin alkoxides and dialkyltin diesters. That patent recommends that maximum dehydration is achieved before addition of the catalyst to the reactants.

U.S. Pat. No. 7,528,278 teaches a transesterification process that involves reacting certain alcohols with an alkyl (meth)acrylate in the presence of a mixed salt catalyst under specified conditions. The mixed salt catalyst can tolerate up to 3,000 ppm water. The patent teaches that prior art catalysts, such as dibutyl tin oxide and lithium hydroxide, are subject to deactivation in the presence of water, and that maximum dehydration of the contents of the reaction vessel should be achieved before addition of said catalysts.

EP-A1-1 686 118 discloses a transesterification process comprising preparing a reaction mixture of alcohol, alkyl (meth)acrylate and polymerization inhibitor, removing water until the water content of the mixture is no more than 1200 ppm, adding at least 2 charges of catalyst, and heating the mixture to commence the reaction.

It would be desirable to have a higher productivity process where the catalyst could be present with higher amounts of water.

SUMMARY OF THE INVENTION

The invention is such a process comprising:
a) forming a mixture by admixing:
a1) reactant alkyl (meth)acrylate;
a2) from 10 to 10,000 parts per million by weight, based on the weight of the reactant alkyl (meth)acrylate, of a free radical polymerization inhibitor; and
a3) optionally, a reactant alcohol and/or a catalyst:
b) if the mixture contains more than 1.1 weight percent water, then dehydrating the mixture so that it contains from 0.2 to 1.1 weight percent water, based on the weight of the mixture;
c) adding reactant alcohol and/or catalyst to the mixture, as needed, such that the molar ratio of reactant alcohol to reactant alkyl (meth)acrylate is from 1:1 to 1:20, and such that the catalyst is present in a catalytic amount;
d) reacting the reactant alcohol with the reactant alkyl (meth)acrylate in a reaction zone at a temperature of from 70 to 125° C. and a pressure of from 100 mm Hg (13.3 kPa) to 900 mm Hg (120.0 kPa), with the proviso that the water content in the reaction zone at the start of this step is from 0.2 to 1.1 weight percent, based on the weight of the materials in the reaction zone;
e) creating a crude product by removing a mixture of alkyl (meth)acrylate and alcohol;
f) optionally adding water to enable recycling of the catalyst;
g) optionally recycling the reactant alkyl (meth)acrylate; and
h) optionally distilling the crude product.

Surprisingly, the catalyst is not inactivated in the presence of from 0.2 to 1.1% water, thereby allowing the process to operate with unexpectedly reduced cycle times. An additional advantage of the process is that less energy is consumed by the process.

DETAILED DESCRIPTION OF THE INVENTION

The process of the invention produces a (meth)acrylate ester product, and in one embodiment involves a first step of forming a mixture which comprises a alkyl(meth)acrylate reactant, an alcohol reactant, a catalyst, and a polymerization inhibitor. The mixture can be subjected to reaction conditions sufficient to produce a product (meth)acrylate and a product alcohol, which are different than the reactants.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth) acrylic acid" refers to either acrylic acid or methacrylic acid.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

The alkyl(meth)acrylate reactant advantageously has the following Formula I:

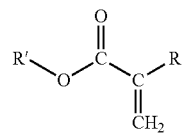

wherein R is H or $CH_3$; and wherein R' is a $C_1$-$C_4$ straight or branched alkyl moiety. In one embodiment of the invention, R and R' are both methyl. Mixtures of alkyl(meth)acrylate reactant can be employed.

Several alcohols are suitable as the reactant alcohol in the process of the invention and include, for example, without limitation: aliphatic linear and branched chain monoalcohols such as, for example, n-butanol, n-propanol, lauryl alcohol, stearyl alcohol, 2-ethylhexanol; cycloaliphatic alcohols, such as cyclohexanol; aromatic alcohols, such as benzyl alcohol; alcohols bearing other functional groups, such as ethylene glycol monomethylether, ethylene glycol monoisopropylether; and alcohols of ethylene oxide adducts of ethylene urea, such as hydroxyethyl ethylene urea (HEEU). Examples of preferred alcohols include HEEU, ethoxylated cetyl stearyl alcohol, such as CSA-20, ethoxylated lauryl myristyl alcohol, dicyclopentenyloxyethyl alcohol, and hydroxyethyl oxazolidine. Advantageously, R'''OH represents the alcohol reactant, where R''' is a substituted or unsubstituted straight chain, branched chain, cyclic, or heterocyclic alkyl moiety, or any combination thereof. For example, R''' may contain heteroatoms such as nitrogen, phosphorous, oxygen, and/or sulfur, and may contain, for example amide, carbonyl, ester, phosphonate, amine, alcohol, and aldehyde functionalities. In addition, R''' may also contain alkenyl or alkynyl functionalities as part of the structure, and may also contain aromatic rings. Mixtures of alcohols can be employed.

The catalyst advantageously is selected from dibutyl tin oxide; reaction products of dibutyl tin oxide with components in the transesterfication of various alcohols with alkyl (meth) acrylates, such as methyl meth(acrylate); dibutyl tin dimethoxide; reaction products of dibutyl tin dimethoxide with components in the transesterification of various alcohols with alkyl (methacrylates); methanolic magnesium methylate; lithium, lithium carbonate, and lithium hydroxide; anhydrous alkali metal hydroxides; hydrates of alkali metal hydroxides; and mixtures thereof. Dibutyl tin oxide is preferred. In one embodiment of the invention, the catalyst is substantially free of chloride and/or fluoride salts. The catalyst is employed in a catalytic amount, i.e. an amount that is at least sufficient to catalyze the reaction of the alcohol with the alkyl(meth)acrylate. The amount of the catalyst added to the reaction vessel advantageously is from 0.1 to 10 mole percent, preferably from 0.5 to 7 mole percent, and more preferably from 1 to 5 mole percent, based on the weight of the alcohol charge.

Suitable polymerization inhibitors include oxygen, diethylhydroxylamine, p-methoxy phenol, hydroquinone, phenothiazine, 2,6-di-t-butylpara-cresol, 3,5-di-t-butyl-4-hydroxyanisole, 2,5-di-t-butylhydroxyanisole, 4-hydroxy-2,2,6,6-tetramethyl piperidinyl free radical (4-hydroxy-TEMPO), 4-methacryloyloxy-2,2,6,6-tetramethyl piperidinyl free radical, and 4-hydroxy-2,2,6,6-tetramethyl N-hydroxy piperidine and mixtures thereof. The total amount of polymerization inhibitor added to the reaction mixture advantageously ranges from lower limits of 10, 100, and 200 to upper limits of 10,000, 5,000, and 3,000 parts per million (ppm) based on the weight of the alkyl(meth)acrylate reactant charge. All ranges used herein are inclusive and combinable. Mixtures of inhibitors can be employed.

Typically, the amount of alkyl(meth)acrylate reactant in the reaction mixture is in stoichiometric excess of the amount of alcohol reactant. For example, the molar ratio of alcohol to alkyl(meth)acrylate advantageously may be from 1:1 to 1:20 or, for example, from 1:2 to 1:6.5, or even from 1:2.2 to 1:3.6. This is because, as discussed in further detail hereinafter, a product alcohol is removed, along with a portion of the alkyl (meth)acrylate reactant, from the reaction mixture by distillation during the period of reaction. In one aspect the product alcohol is removed, along with a portion of the alkyl(meth) acrylate reactant, from the reaction mixture by azeotropic distillation. The removed mixture of alkyl(meth)acrylate and product alcohol may be further separated and the alkyl(meth) acrylate reactant may be recycled to the reaction mixture.

If one desires to remove water from the mixture, it is possible, as described hereinabove, to combine the alkyl (meth)acrylate, the catalyst, the alcohol and the polymerization inhibitor, to form a mixture and then remove water from this mixture. Alternatively, it is also possible to combine the alkyl(meth)acrylate, the catalyst, and the polymerization inhibitor, remove water therefrom, and then add the alcohol thereto, thus forming a reaction mixture. In one embodiment of the invention, it is also possible to combine the alkyl(meth) acrylate, the alcohol, and the polymerization inhibitor, remove water therefrom, and then add the catalyst thereto, thus forming a reaction mixture. In one embodiment of the invention, it is possible to combine all components of the mixture prior to dehydration. The step of removing water from the reaction mixture may be accomplished, for example, without limitation, by azeotropic distillation of a mixture of water and alkyl(meth)acrylate.

Advantageously, unreacted alkyl(meth)acrylate can be recycled and can contain residual amounts of water such as, for example, from 1.25 to 3 weight percent, based on the weight of water and alkyl(meth)acrylate. The process of the invention advantageously involves dehydrating the reaction mixture so that it contains from 0.2 to 1.1 weight percent water, based on the weight of the reaction mixture, at the start of the reaction.

In one aspect of the present invention, only one charge of catalyst is added. The catalyst charge comprises an amount of catalyst equal to from 0.1 to 10 mole %, preferably from 1-2 mol % based on the total moles of alcohol that are present, or which will be present, in the reaction mixture, depending upon which of the foregoing methods of forming the reaction mixture is practiced. The catalyst can be added by any known, conventional delivery means, such as, without limitation, via a pressurized or unpressurized charge hopper, or via a parallel series of individually controlled inline chambers where the catalyst is mixed with the reaction mixture as a carrier, or into a slurry mix with, for example, methyl methacrylate. In one embodiment of the invention, the catalyst is added in multiple charges.

The reaction temperature (i.e., the temperature of the reaction mixture during the transesterification reaction) of the process may be from about 60° C. to 140° C., for example, without limitation, from 70° C. to 125° C., or from 85° C. to 100° C. The reaction pressure may be from 760 mm Hg (atmospheric) (101.3 kPa) to reduced or elevated pressures, such as, for example, from 100 mm Hg (13.3 kPa) to 900 mm Hg (120.0 kPa). As known to those skilled in the art, the reaction temperature can be adjusted as the pressure varies from atmospheric pressure.

As the transesterification reaction proceeds, the products include, but are not necessarily limited to, a product (meth) acrylate and a product alcohol that is different from the reactant alcohol employed to form the reaction mixture. The product (meth)acrylate ester produced by the transesterification process of the present invention advantageously has Formula II as follows:

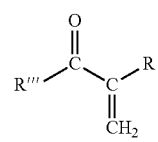

wherein R is H or CH$_3$, and R''' is as described hereinabove. The product alcohol has Formula III as follows:

where R' is as described hereinabove.

For example, when the reactant alcohol is a hydroxyl alkyl imidazolidin-2-one, having the following Formula IV:

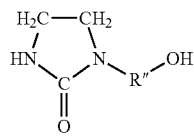

wherein R'' is a C$_1$-C$_8$ straight, branched or cyclic, and saturated or unsaturated, hydrocarbon moiety, then the product (meth)acrylate ester has Formula V as follows:

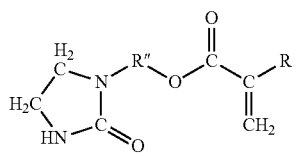

wherein R is H or CH$_3$, and R'' is a C$_1$-C$_8$ straight, branched or cyclic, saturated or unsaturated, hydrocarbon moiety.

During the course of the reaction, the product alcohol advantageously is removed from the system, by azeotropic distillation, as an azeotropic mixture of the alkyl(meth)acrylate reactant and the product alcohol.

Particular embodiments of the process of the present invention will now be described in detail in connection with the following examples.

SPECIFIC EMBODIMENTS OF THE INVENTION

The following examples are given to illustrate the invention and should not be construed as limiting its scope. All parts and percentages are by weight unless otherwise indicated.

EXAMPLES

Comparative Experiment 1

Not an Embodiment of the Invention

The following experiment demonstrates cycle time under the baseline conditions of dehydrating to <0.1% water.

A mixture of 8.30 grams (0.0333 moles) of dibutyltin oxide catalyst (DBTO), 520 grams (5.09 moles) of methyl methacrylate (MMA), with 2% water added to simulate recycled MMA, and 0.7 grams (0.0040 moles) of 4-hydroxy TEMPO is charged to a 1-liter 4-necked flask equipped with a temperature indicator/controller/magnetic stirrer (Heidolph MR Hei-standard, available from Fisher Scientific, Pittsburgh, Pa. 15275), mixed gas (8% O$_2$-92% N$_2$) sparge inlet, and a 1 inch diameter-15 plate Oldershaw column fitted with a magnetically controlled distillation head, controlled by a repeat cycle timer (ACE Glass 6671-14 repeat cycle timer continuous 1 to 6000 seconds, available from ACE Glass, Vineland, N.J. 08362), and a graduated distillate receiver. During dehydration of the batch, the mixture is stirred, sparged with mixed gas at a rate of 1 ml/min and heated to reflux at atmospheric pressure, while removing the MMA-water azeotrope. The overhead splitter is set to send 75% of the distillate forward and 25% back to the column. The maximum temperature atop the column is 99° C. and the maximum temperature in the flask is 105° C. The mixture is dehydrated to a water concentration of <0.10%. Distillation is stopped by turning off the overhead splitter so that no distillate is sent forward, and to the reaction mixture is added 220 grams (1.69 moles) of HEEU. Within 15 minutes of adding HEEU, the overhead temperature equilibrates to about 68-70° C. and the distillation is resumed by turning on the overhead splitter and sending 25% of the distillate forward and 75% back to the column During the subsequent reaction step, the mixture is stirred, sparged with mixed gas, and is continuously heated to reflux at atmospheric pressure while removing the MMA-methanol of reaction azeotrope. The reaction is considered complete when the HEEU concentration is less than 3.5%, at which point the distillation is halted by turning off the overhead splitter so that no distillate is sent forward.

A final product formulation is then prepared by performing a water transfer of the excess methyl methacrylate, as follows. The mixture is cooled to 60-70° C. and about 300 grams of water is added. The flask contents are heated, under a reduced pressure of 150 mm Hg, the overhead splitter is turned on to send 75% of the distillate forward and 25% back to the column, and the MMA-water azeotrope is removed. During the removal of excess MMA the contents are stirred and sparged. The catalyst is removed via filtration. The procedure is repeated 3 times. The filtered product mixture is a clear yellow liquid. According to quantitative high-performance liquid chromatography (HPLC), the mixtures from the 3 runs contain 50-52 weight % MEEU, 1-3.5 weight % HEEU, and 0.7-0.8 weight % N-(2-methacryloyloxyethyl)-N'-(methacryloyl)ethylene urea (MEMEU) and 0.2-0.8 weight % of MMA. By Karl Fischer analysis the product contains 40-48 weight % water. In all cases the weight percentages total 100% for the product mixture.

| The 3 runs have the following cycle times: | | | | |
|---|---|---|---|---|
| | Experiment 1 | Experiment 2 | Experiment 3 | Average |
| Dehydration (min) | 52 | 45 | 65 | 54 |
| Reaction (min) | 255 | 255 | 250 | 253 |
| Water Transfer (min) | 165 | 160 | 190 | 172 |
| Total (min) | 578 | 591 | 615 | 595 |

Dehydration, reaction, and water transfer times are defined by the actual start (first drop) and stop (last drop) of distillation during those steps. Total time is defined as the time elapsed from the initial application of heat prior to dehydration to the time heat is removed at the end of water transfer.

Example 2

This example demonstrates cycle time reduction under the conditions of high water (1%).

Using the equipment of Comparative Experiment 1, a mixture of 8.30 grams (0.0333 moles) of DBTO, 520 grams (5.09 moles) of MMA, with 1% water added to simulate recycled MMA, 0.7 grams (0.0040 moles) of 4-hydroxy TEMPO and 226.0 grams (1.74 moles) of HEEU is charged to the flask. No dehydration step is performed. The mixture is stirred, sparged with mixed gas at a rate of 1 ml/min and heated to reflux at atmospheric pressure, while removing the MMA-methanol azeotrope. The overhead splitter is set to send 25% of the distillate forward and 75% back to the column. The maximum temperature atop the column is 68-70° C. The reaction is considered complete when the HEEU concentration is less than 3.5%, at which point the distillation is halted by turning off the overhead splitter so that no distillate is sent forward.

A final product formulation is then prepared by performing a water transfer of the excess MMA, as follows. The mixture is cooled to 60-70° C. and about 300 grams of water is added. The flask contents are heated, under a reduced pressure of 150 mm Hg, the overhead splitter is turned on to send 75% of the distillate forward and 25% back to the column, and the MMA-water azeotrope is removed. During the removal of excess MMA the contents are stirred and sparged. The catalyst is removed via filtration. The procedure is repeated 3 times. The filtered product mixture is a clear yellow liquid. According to quantitative HPLC, the mixtures from the 3 runs contain 51-53 weight % MEEU, 1-3.5 weight % HEEU, and 0.5-1.1 weight % MEMEU and 0.3-0.8 weight % of MMA. By Karl Fischer analysis the product contains 40-48 weight % water.

| The 3 runs have the following cycle times. | | | | |
|---|---|---|---|---|
| | Experiment 1 | Experiment 2 | Experiment 3 | Average |
| Reaction (min) | 240 | 240 | 270 | 250 |
| Water Transfer (min) | 108 | 105 | 110 | 108 |
| Total (min) | 520 | 525 | 485 | 510 |

Reaction time, water transfer, and total time are defined hereinabove.

A significant cycle time reduction is achieved when doing the reaction in the presence of 1% water. The average cycle time with dehydration to 0.1% water is 595 minutes, while the average cycle time without dehydration (reaction in the presence of 1% water) is 510 minutes. This unexpectedly equates to a 14.3% reduction in cycle time.

As demonstrated by Example 2, the dehydration can be stopped at a higher water level than was previously believed. Surprisingly, the catalyst is not inactivated in the presence of from 0.2 to 1.1% water.

What is claimed is:

1. A process for producing (meth)acrylate monomers, the process comprising:
    a) forming a mixture by admixing:
       a1) reactant alkyl (meth)acrylate;
       a2) from 10 to 10,000 parts per million by weight, based on the weight of the reactant alkyl (meth)acrylate, of a free radical polymerization inhibitor; and
       a3) optionally, a reactant alcohol and/or a catalyst:
    b) if the mixture contains more than 1.1 weight percent water, then dehydrating the mixture so that it contains from 1.0 to 1.1 weight percent water, based on the weight of the mixture;
    c) adding reactant alcohol and/or catalyst to the mixture, as needed, such that the molar ratio of reactant alcohol to reactant alkyl (meth)acrylate is from 1:1 to 1:20, and such that the catalyst is present in a catalytic amount;
    d) reacting the reactant alcohol with the reactant alkyl (meth)acrylate in a reaction zone at a temperature of from 70 to 125° C. and a pressure of from 100 mm Hg (13.3 kPa) to 900 mm Hg (120.0 kPa), with the proviso that the water content in the reaction zone at the start of this step is from 1.0 to 1.1 weight percent, based on the weight of the materials in the reaction zone;
    e) creating a crude product by removing a mixture of alkyl (meth)acrylate and alcohol;
    f) optionally adding water to enable recycling of the catalyst;
    g) optionally recycling the reactant alkyl (meth)acrylate; and
    h) optionally distilling the crude product;
wherein the catalyst is selected from the group consisting of dibutyl tin oxide, lithium carbonate, and lithium hydroxide.

2. The process of claim 1 wherein the alcohol is selected from the group consisting of hydroxyethyl ethylene urea, ethoxylated cetyl-stearyl alcohol, ethoxylated lauryl-myristyl alcohol, dicyclopentenyloxyethyl alcohol, and hydroxyethyl oxazolidine.

3. The process of claim 1 wherein the alcohol is selected from the group consisting of n-butanol, n-propanol, lauryl alcohol, stearyl alcohol, 2-ethylhexanol; cyclohexanol; benzyl alcohol; ethylene glycol monomethylether, and ethylene glycol monoisopropylether.

4. The process of claim 1 wherein the dehydration of step b) is not employed.

5. The process of claim 1 wherein the product alcohol is methanol.

6. The process of claim 1 wherein the reactant alkyl (meth)acrylate is methyl (meth)acrylate.

7. A process comprising:
    a) forming a reaction mixture by admixing methyl methacrylate, a free radical polymerization inhibitor, HEEU and a catalyst comprising DBTO, wherein the reaction mixture further comprises from more than 1.1 to 5 wt. % water, based on the weight of the reaction mixture;
    b) dehydrating the reaction mixture so that it contains from 0.2 to 1.1 weight percent water, based on the weight of the reaction mixture;
    c) reacting the HEEU with the methyl methacrylate in a reaction zone at a temperature of from 70 to 125° C. and a pressure of from 100 mm Hg (13.3 kPa) to 900 mm Hg (120.0 kPa) to produce MEEU and methanol;
    d) creating a crude product by removing a mixture of methyl methacrylate and methanol;
    e) optionally adding water to enable recycling of the catalyst;
    f) optionally recycling the methyl methacrylate; and
    g) optionally distilling the crude product.

8. The process of claim 7 wherein the removal of step d) is conducted by azeotropic distillation.

9. The process of claim 7, wherein the mixture is dehydrated in step b) so that it contains from 1.0 to 1.1 weight percent water, based on the weight of the mixture.

* * * * *